United States Patent [19]
Bremer

[11] Patent Number: 5,718,670
[45] Date of Patent: Feb. 17, 1998

[54] THORACAL LUMBOSACRAL ORTHOSIS FOR A HUMAN TORSO

[76] Inventor: Ross L. Bremer, 1502 Beach Ave., Atlantic Beach, Fla. 32233

[21] Appl. No.: 199,342

[22] Filed: Feb. 18, 1994

[51] Int. Cl.⁶ ............................................. A61F 5/00
[52] U.S. Cl. ................................................... 602/19
[58] Field of Search ...................... 602/18, 19; 2/2.5, 2/44

[56] References Cited

U.S. PATENT DOCUMENTS

| | | | |
|---|---|---|---|
| 3,871,367 | 3/1975 | Miller | 602/19 |
| 4,202,327 | 5/1980 | Glancy | 602/19 |
| 4,230,101 | 10/1980 | Gold | 602/19 |
| 4,285,336 | 8/1981 | Oebser et al. | 602/19 |
| 4,508,110 | 4/1985 | Modglin | 602/19 |
| 4,688,558 | 8/1987 | Hooper, Jr. et al. | 602/19 |
| 4,930,499 | 6/1990 | Rowe | 602/19 |
| 5,158,531 | 10/1992 | Zamosky | 602/19 |

FOREIGN PATENT DOCUMENTS

| | | | |
|---|---|---|---|
| 99783 | 2/1984 | European Pat. Off. | 602/19 |

OTHER PUBLICATIONS

"Save Yourself Time and Money . . . " brochure, National Orthotic Laboratories, Winter Haven, Florida.

*Primary Examiner*—Linda C. Dvorak
*Attorney, Agent, or Firm*—Nixon & Vanderhye

[57] ABSTRACT

A thoracal lumbosacral orthosis includes an anterior panel and a posterior panel for overlying anterior and posterior trunk portions of a patient's torso. The panels are strapped one to the other along opposite side edges and about a patient's torso. The anterior panel has an upper edge having a central arcuate concave recess and a pair of lateral arcuate concave recesses straddling the central recess to prevent discomfort or injury to the patient's neck upon lumbosacral flexion and facilitating shoulder movement, respectively. An opening is formed in the anterior panel overlying the diaphragm region of the patient to facilitate patient respiration. The posterior panel has an opening overlying the spine of the patient. This posterior opening is closed with a flexible, preferably foam, material, such that only light pressure is applied to a spinal surgical site in response to attempted movements by the patient or expansion, e.g., swelling, of the surgical site.

3 Claims, 2 Drawing Sheets

5,718,670

THORACAL LUMBOSACRAL ORTHOSIS FOR A HUMAN TORSO

TECHNICAL FIELD

The present invention relates to a thoracal lumbosacral orthosis body jacket for the torso of a human patient for controlling lumbosacral flexion and extension, lateral flexion and certain rotary movements for stabilization of the spine.

BACKGROUND

There are many instances when it is necessary or desirable to stabilize the spine. For example, it is necessary after spinal surgery for spinal fusion, cancer, tumor, or for spinal decompression, to stabilize the Is spine and substantially prevent or control the movement of the spine in flexion, extension and certain rotary movements. Further examples might include post-operative idiopathic and non-idiopathic scoliosis, stabilization of an osteoporotic spine and stabilization of vertebral fractures where non-neurological deficit has been incurred and surgery is contraindicated.

Body jackets for purposes of stabilizing the spine are known in the prior art and typically comprise panels secured to one another overlying anterior and posterior trunk portions of the patient's torso. Many such body jackets provide undesirable pressure points on the patient's body, do not provide full shoulder motion or facilitate patient respiration and frequently cause the patient pain upon attempted flexion, extension or rotary movements. Further, most body jackets, to applicant's knowledge, do not accommodate the surgical site and simply overlie the site with a relatively hard material such that pressure is oftentimes applied to the site. Expansion of the surgical site, for example, by swelling, similarly cannot be accommodated.

DISCLOSURE OF THE INVENTION

According to the present invention, there is provided a thoracal lumbosacral orthosis body jacket for the torso of a human patient, which facilitates patient respiration, affords full shoulder motion, prevents injury to the patient as well as pain upon attempted lumbosacral flexion, extension and rotary movements, affords an expandable, flexible overlay for the surgical site which prevents pressure from being applied to the site and enables expansion of the site as necessary to accommodate swelling and simultaneously affords complete stabilization of the spine. To accomplish the foregoing, there is provided a body jacket comprised of an anterior panel and a posterior panel contoured in a three-dimensional sense to accommodate the anterior and posterior trunk portions of the patient's torso. The anterior and posterior panels are secured to one another along their registering side edges, preferably by Velcro™ straps. The anterior panel includes a shaped upper or top edge which precludes interference between the anterior panel and neck and shoulder regions of the patient's torso in response to attempted lumbosacral flexion. Particularly, the top central edge of the anterior panel has an arcuate concave recess such that, upon attempted lumbosacral flexion, the anterior panel does not interfere with the patient's neck. A pair of arcuate concave recessed edges lie on opposite sides of the central recess and along the top edge of the panel to accommodate shoulder movement. Additionally, the anterior panel of the body jacket hereof includes an opening which has an interior edge generally coincident with or outside the margin of the patient's diaphragm. The opening therefore facilitates patient respiration, while simultaneously the anterior panel has sufficient strength, in conjunction with the posterior panel, to prevent lumbosacral flexion, extension and rotary movements. A still further feature of the present invention provides an opening within the posterior panel at a location for overlying the spinal region of the patient's torso. This interior opening is covered with a flexible material, such as an expanded polyethylene closed cell foam. The opening and the foam covering therefor is intended to overlie a spinal surgical site and prevent the application of pressure from the body jacket to the surgical site in response to body movements by the patient. Additionally, the flexible foam material enables enlargement of the surgical site such as, for example, by swelling, without bearing against the rigid material of the posterior panel.

In a preferred embodiment according to the present invention, there is provided thoracal lumbar sacral orthosis for the torso of a human patient, comprising an anterior panel contoured for overlying an anterior trunk portion of the patient's torso and having top, side and bottom edges, a posterior panel contoured for overlying a posterior trunk portion of the patient's torso and having top, side and bottom edges, means o carried by the panels along the side edges thereof for securing the anterior and posterior panels to one another in overlying relation to anterior and posterior portions, respectively, of the patient's trunk, the anterior panel having a shaped top edge including a recessed top central edge portion and a pair of recessed lateral edge portions on opposite sides of the recessed top central edge portion to preclude interference between the anterior panel and neck and shoulder regions of the patient's torso in response to attempted lumbosacral flexion.

In a further preferred embodiment according to the present invention, there is provided a thoracal lumbar sacral orthosis for the torso of a human patient, comprising an anterior panel contoured for overlying an anterior trunk portion of the patient's torso and having top, side and bottom edges, a posterior panel contoured for overlying a posterior trunk portion of the patient's torso and having top, side and bottom edges, means carried by the panels along the side edges thereof for securing the anterior and posterior panels to one another in overlying relation to anterior and posterior portions, respectively, of the patient's trunk and an endless interior edge portion of the anterior panel defines an opening in the anterior panel located to generally overlie a region of the patient's diaphragm to facilitate patient respiration.

In a further preferred embodiment according to the present invention, there is provided a thoracal lumbar sacral orthosis for the torso of a human patient, comprising an anterior panel contoured for overlying an anterior trunk portion of the patient's torso and having top, side and bottom edges, a posterior panel contoured for overlying a posterior trunk portion of the patient's torso and having top, side and bottom edges, means carried by the panels along the side edges thereof for securing the anterior and posterior panels to one another in overlying relation to anterior and posterior portions, respectively, of the patient's trunk, the posterior panel having an interior edge portion defining an opening for overlying a patient's spinal region, and a flexible material carried by the posterior panel in the opening for overlying the patient's spinal region.

Accordingly, it is a primary object of the present invention to provide a novel and improved thoracal lumbosacral orthosis for limiting lumbosacral flexion and extension, lateral flexion and certain rotary movements of a patient and in a manner which facilitates patient respiration, minimizes or eliminates discomfort to the patient caused by interaction of the body jacket and patient in response to body movements and provides a flexible covering within the rigid posterior panel of the body jacket for overlying and preventing pressure on the spinal surgical site by the posterior panel in response to body movements and enabling a surgical site to expand against, for example, by swelling, the panel without responsive pressure applied to the surgical site.

BEST MODE FOR CARRYING OUT THE INVENTION

Figure 2:
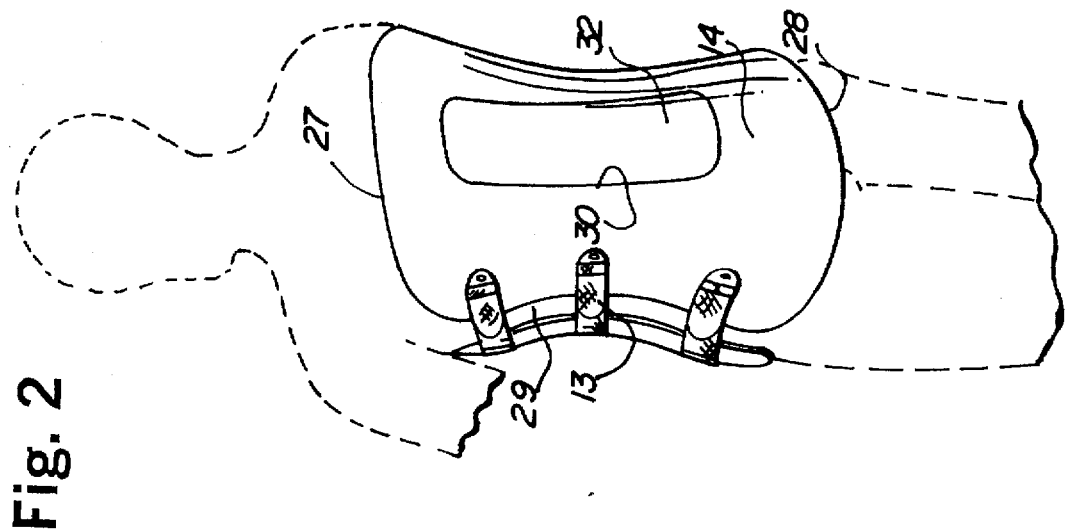
FIG. 2 is a perspective view of the body jacket according to FIG. 1 illustrating primarily the posterior panel of the jacket.

Referring now to the drawing figures, there is illustrated a thoracal lumbosacral orthosis body jacket for overlying the torso of a human patient, the orthosis being generally indicated at 10. Orthosis 10 includes a front or anterior body panel 12 and a back or anterior body panel 14 for overlying the anterior and posterior trunk portions of the human torso. Each panel is generally contoured to the shape of the human torso, i.e., the anterior trunk and posterior trunk portions of the torso, to provide as comfortable a fit as possible given that the panels are formed of a substantially rigid material. By contoured, it is meant that the shape of the panel is three-dimensional and generally follows the three-dimensional contour of the human trunk in registry with the interior surfaces of the panels. Each panel is formed preferably of a plastic material, for example, a molded polyethylene. The thickness of the material may range from 3/16–3/8 inch, depending upon the size of the jacket being provided. It will also be appreciated that various sizes of jackets may be provided, for example, small, medium and large, or sizes in-between, to accommodate the torsos of individuals of different sizes including variations in height and girth.

The anterior and posterior panels are secured on opposite sides 15 of the trunk portion of the patient's torso by straps 13 interconnecting the side edges of the panels. While many different types of fasteners may be employed to secure the panels about the torso, Velcro™-type straps are preferred. One end of each strap is accordingly secured to one of the panels, preferably with screws and T-headed nuts formed along the inside of the panel and lying flush with the interior surface therewith. The straps, of course, extend to mating portions of the Velcro™ fastener secured on the opposite panel.

Figure 1:
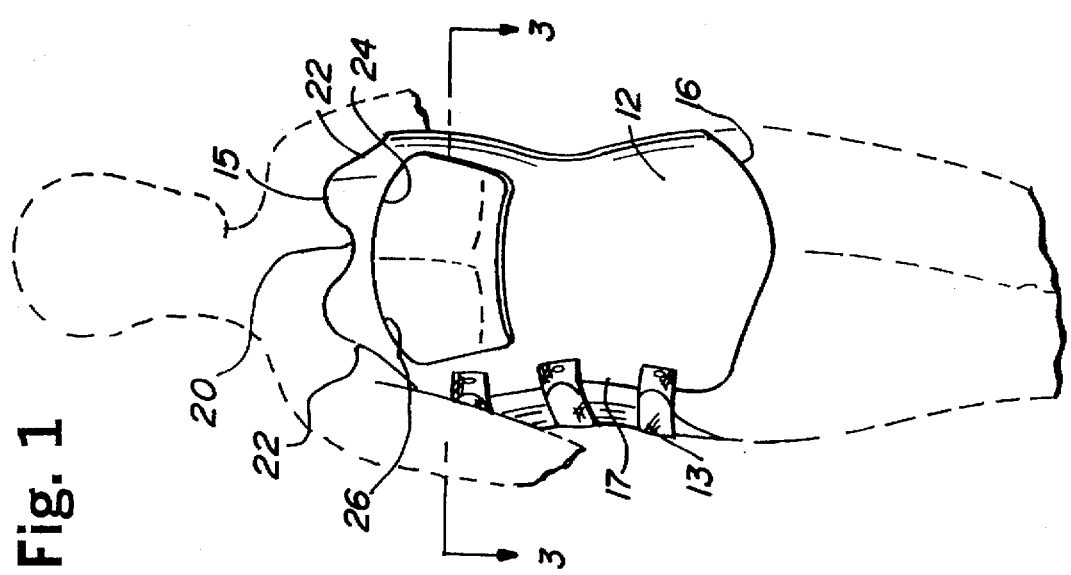
FIG. 1 is a perspective view illustrating a thoracal lumbosacral orthosis body jacket according to the present invention and particularly the anterior panel thereof applied to the torso of a human patient.
Figure 3:
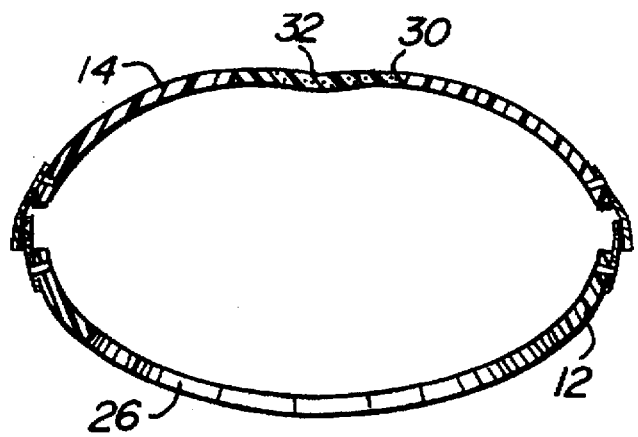
FIG. 3 is a cross-sectional view thereof taken generally about on line 3—3 in FIG. 1.
Figure 4:
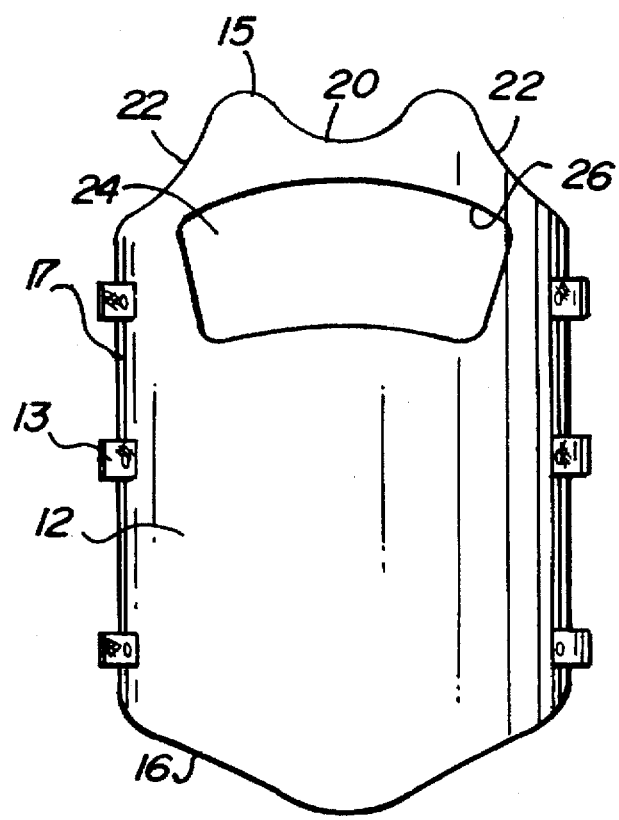
FIG. 4 is a front elevational view of the anterior panel.

In accordance with the present invention, the anterior panel 12, as illustrated in FIG. 1, has top, side and bottom edges 15, 16 and 17, respectively, the top edges 15 being particularly shaped to prevent discomfort or injury to the patient upon attempted lumbosacral flexion and lateral flexion, while simultaneously enabling some shoulder movement. To this end, the top edge of the anterior panel has a recess 20 along a central portion thereof and a pair of recessed lateral edge portions 22 on opposite sides of the recessed top central edge portion. Each of the recessed portions constitute an arcuate concave edge. In this manner, the centrally located top recess does not bear against or engage the patient's neck upon attempted lumbosacral flexion. The concave arcuate lateral recesses 22 afford some shoulder movement, while simultaneously preventing discomfort to the patient.

According to another aspect of the present invention, there is provided an opening 24 in the anterior panel which is located generally to overlie the region of the patient's diaphragm to facilitate patient respiration. The endless interior edge portions 26 of the opening 24 thus generally follow or lie outside of the general outline of the patient's diaphragm as projected anteriorly. This opening facilitates the breathing function and particularly the expansion and contraction of the trunk in the region of the diaphragm caused by patient respiration.

Referring now to FIG. 2, the posterior panel 14 similarly has top, side and bottom edges 27, 28 and 29, respectively, and also a central opening 30. As illustrated, the opening 30 is centrally located in the posterior panel and extends vertically to overlie the spinal region of the patient. Attached to the posterior panel 14 is a flexible material 32 which closes the opening 30. The flexible material is preferably a foam material, such as an expanded closed cell polyethylene foam. Consequently, while the material of the posterior panel 14 surrounding the flexible material is a relatively hard inflexible plastic, the flexible material 32 overlies the spinal region and particularly an operative site, for example, a site where spinal fusion has been surgically performed. The flexible panel 32 consequently does not apply pressure to the operative site or to the underlying spine upon attempted flexion or extension or rotary movements of the patient's torso. Moreover, the flexible nature of the material permits expansion of the surgical site, such as by swelling, without forming a pressure point on the patient's body at that site caused by any bearing engagement of the hard surface of the posterior panel 14.

Accordingly, it will be appreciated that the objects of the present invention have been fully accomplished in that there has been provided a thoracal lumbosacral orthosis for (i) controlling the movements of the patient's spine in flexion, extension, lateral flexion and certain rotary movements, i.e., stabilizing the spine, while simultaneously preventing discomfort or injury to the patient upon attempted body movement, (ii) facilitating patient respiration and (iii) affording the capability to have only light pressure on the surgical site while simultaneously controlling the movement of the patient.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A thoracal lumbar sacral orthosis for the torso of a human patient, comprising:

a discrete anterior panel contoured for overlying an anterior trunk portion of the patient's torso and having a continuous periphery thereabout with peripheral top, side and bottom edges;

a discrete posterior panel contoured for overlying a posterior trunk portion of the patient's torso and having peripheral top, side and bottom edges;

means carried by said panels along sides thereof for securing said anterior and posterior panels to one another in overlying relation to anterior and posterior portions, respectively, of the patient's trunk;

said posterior panel having an interior edge portion defining an opening for overlying a patient's spinal region, and a flexible foam material carried by said posterior panel in said opening for overlying the patient's spinal region without applying pressure to the underlying patient's spinal region upon attempted flexion, extension or rotary movements of the patient's torso;

said anterior panel having along said edges thereof a recessed concave top central edge and a pair of recessed concave lateral edges on opposite sides of said recessed top central edge to preclude interference between the anterior panel and neck and shoulder regions of the patient's torso in response to attempted lumbosacral flexion, and an opening in the anterior panel defined by an endless interior peripheral edge and located to generally overlie a region of the patient's diaphragm to facilitate patient respiration.

2. An orthosis according to claim 1 wherein said foam material comprises an expanded, closed cell, polyethylene foam.

3. An orthosis according to claim 1 wherein said interior edge of said anterior panel generally follows the outline of the patient's diaphragm.

* * * * *